United States Patent [19]

Urayama et al.

[11] Patent Number: 4,901,171

[45] Date of Patent: Feb. 13, 1990

[54] OPTICAL TAPE END SENSING ARRANGEMENT FOR MAGNETIC TAPE CASSETTE

[75] Inventors: Kiyoshi Urayama; Shinya Sato; Yuji Iwahashi, all of Miyagi, Japan

[73] Assignee: Sony Corporation, Tokyo, Japan

[21] Appl. No.: 174,206

[22] Filed: Mar. 28, 1988

[30] Foreign Application Priority Data

Apr. 6, 1987 [JP] Japan ................... 62-084462

[51] Int. Cl.⁴ ............................................. G11B 5/22
[52] U.S. Cl. ..................................... 360/74.6; 360/132
[58] Field of Search ............... 360/132, 74.6; 242/198

[56] References Cited

U.S. PATENT DOCUMENTS

| | | | |
|---|---|---|---|
| 4,363,059 | 12/1982 | Matsuzawa et al. | 360/74.6 |
| 4,644,433 | 2/1987 | Horikawa et al. | 360/132 |
| 4,740,857 | 4/1988 | Ogawa | 360/132 |

FOREIGN PATENT DOCUMENTS

| | | |
|---|---|---|
| 0045327 | 10/1982 | European Pat. Off. . |
| 0157201 | 10/1985 | European Pat. Off. . |
| 3315167 | 11/1983 | Fed. Rep. of Germany . |
| 3510874 | 10/1986 | Fed. Rep. of Germany . |
| 57-26779 | 2/1982 | Japan . |
| 60-102787 | 7/1985 | Japan . |
| 60-236177 | 11/1985 | Japan . |
| 2119751 | 11/1983 | United Kingdom . |
| 2145999 | 4/1985 | United Kingdom . |

*Primary Examiner*—Robert S. Tupper
*Attorney, Agent, or Firm*—Ronald P. Kananen

[57] ABSTRACT

A tape cassette arrangement includes structures formed integrally with the cassette halves or simply fitted into the light transmission apertures. Specific embodiments of the invention include light polarizing elements which are fitted into apertures formed in the sides of the cassette, corrugations on the interior of the cassette proximate the apertures, and shielding walls which are located to block light and in particular that light which tends to enter through a large window provided in the upper surface of the cassette and through which the status of the tape is visible.

29 Claims, 22 Drawing Sheets

OPTICAL TAPE END SENSING ARRANGEMENT FOR MAGNETIC TAPE CASSETTE

BACKGROUND OF THE INVENTION

1. Field of the Invention

The present invention relates generally to a cassette for use in recording and reproducing devices and more specifically to a cassette which is arranged to provide accurate tape end detection, which is simple in construction and which can be made of a brightly coloured material.

2. Description of the Prior Art

In a previously proposed cassette arrangement such as shown in FIG. 1, in order to detect the end of the tape being approached it has been proposed to add a transparent leader tape section to each end of the magnetic tape and arrange for a light source "e" to be introduced into the cassette, and dispose light responsive sensors "g" in positions wherein, when an end of the tape is being approached and the leader tape at that end begins to unwind from one of the two tape reels, the light from the light source "e" is able to pass through the transparent leader tape, pass out through a light transmission aperture "b" and be received by one of the sensors or pickups "g".

With this arrangement it is possible to timely stop the motor mechanism which drives the tape reels prior to the actual end of the tape being completely reached and avoid damage to or breakage of to the tape due to the continued application of torque to the take up reel when the tape has been completely wound thereonto.

However, this arrangement has suffered from the drawback that erroneous detection of the tape end tends to occur and result in the operation of the tape drive being stopped prematurely. The reason for this erroneous detection has been found to be due to light, which enters the cassette such as through the window section, provided for visually ascertaining how much tape is wound on each reel, is sometimes reflected on the internal structure of the cassette and/or the magnetic tape and a light ray such as denoted by "d" is directed toward one of the light transmission apertures "b" formed in the side wall of the housing. This light ray propagates along a path sufficiently close to line "f" (along which the light beam emitted from the light source "e" is transmitted) to be received by a sensor "g" in a manner that triggers an erroneous tape end signal.

In order to overcome this problem it has been proposed in JP-A-57-26779 to, in addition to the common technique of making the cassette case of a dark coloured material which exhibits low reflectivity, form one or more portions of the window section through of the cassette case of a semi-transparent material in an effort to diffuse the light entering the interior of the cassette.

In JP-A-60-236177 it has been proposed to provide the upper surface of the lower flange of the tape reels with mat surfaces in order to reduce the amount of light which is reflected thereoff.

However, neither of these arrangements has proven sufficiently satisfactory.

In JP-A-60-102787 it has been proposed to add a so called "lock plate" arrangement to the cassette. This arrangement includes a "tunnel" section through which the light which reaches the sensors or pick-ups must pass. However, this construction has suffered from the drawbacks that the length of the tunnel sections must be quite long in order to adequately screen out the reflected light rays which will induce erroneous tape end signals and thus obviates its use in smaller type cassettes wherein sufficient space is not available. Further, this arrangement due to its disposition and orientation cannot be formed integrally with the cassette and must be added as a separate unit. Installation of the unit must be made carefully so as to ensure proper operation. This of course adds to the number of assembly operations and therefore to the cost of the device. In addition to this, the lock plate member itself requires the inclusion of a metallic slide member which further increases the production costs.

SUMMARY OF THE INVENTION

It is an object of the present invention to provide a cassette construction which is simple, easily assembled with the minimum number of operations and which further allows the cassette to be formed of a bright coloured material.

In brief the above object is achieved by a tape casette arrangement which includes structures formed integrally with the casssette halves or simply fitted into the light transmission apertures. Embodiments of the invention include light polarizing elements which are fitted into apertures formed in the sides of the cassette, corrugations on the interior of the cassette proximate the apertures, and shielding walls which are located to block light and in particular that light which tends to enter through a large window provided in the upper surface of the cassette and through which the status of the tape is visible.

More specifically, a first aspect of the present invention comes in the form of a tape cassette which features: means for housing a light source; means defining a light transmission aperture in a wall portion of cassette housing; means associated with said light transmission aperture for preventing light which does not come directly from the light source from passing through said light transmission aperture, said light passage preventing means being one of formed integrally with the cassette housing and disposed in said light transmission aperture.

A second aspect of the invention takes the form of a tape cassette which features: means for housing a light source; means defining a light transmission aperture in a wall portion of cassette housing; a tape reel on which a tape is wound, said tape having a section which is transparent to the light emitted from said light source; means associated with said light transmission aperture for attenuating light which does not come directly from the light source and pass through said transparent section in a manner that it does not pass through said light transmission aperture and reach a sensor disposed outside of the cassette in a manner which triggers the sensor to produce a signal, said light attenuating means being one of (a) formed integrally with the cassette housing and (b) disposed in said aperture.

A third aspect of the invention comprises a cassette for use in a device which is equipped with a light source and a sensor responsive to the light emitted from said light source, said cassette comprising: a first half; a second half, said second half being connectable to said first half in a manner to define a housing, one of said upper and lower halves being formed with a structure into which said light source can be selectively introduced; at least one tape reel disposed in said housing; magnetic tape wound on said at least one tape reel; a leader tape connected at one end to said at least one tape reel and to the magnetic tape at the second end, said leader tape being transparent to the light emitted from said light source; means defining a light transmission aperture in the housing defined said upper and lower halves when connected; a structure for attenuating light which does not come directly through said leader tape from said light source and which tends to pass through said light transmission aperture toward said sensor, said structure comprising: two wall portions which project from opposed sides of said light transmission aperture, said wall portions being formed integrally with one of said upper and lower halves, said wall portions extending essentially in the direction of the structure into which the light source can be selectively introduced.

A fourth aspect of the invention takes the form of a cassette for use in a device which is equipped with a light source and a sensor responsive to the light emitted from said light source, said cassette comprising: a first half; a second half, said second half being connectable to said first half in a manner to define a housing, one of said upper and lower halves being formed with a structure into which said light source can be selectively introduced; at least one tape reel disposed in said housing; magnetic tape wound on said at least one tape reel; a leader tape connected at one end to said at least one tape reel and to the magnetic tape at the second end, said leader tape being transparent to the light emitted from said light source; means defining a light transmission aperture in the housing defined by said upper and lower halves when connected; means defining a window in one of said upper and lower halves through which said tape reel is visible; a structure for attenuating light which does not come directly through said leader tape from said light source and which tends to pass through said light transmission aperture toward said sensor, said structure comprising: a wall portion which is formed integrally with one of said upper and lower halves and which is disposed between said window and said light transmission aperture for preventing the transmission of light which enters the interior of said cassette through said window from propagating toward said light transmission aperture.

Another aspect of the invention comprises a cassette for use in a device which is equipped with a light source and a sensor responsive to the light emitted from said light source, said cassette comprising: a first half; a second half, said second half being connectable to said first half in a manner to define a housing, one of said upper and lower halves being formed with a structure into which said light source can be selectively introduced; at least one tape reel disposed in said housing; magnetic tape wound on said at least one tape reel; a leader tape connected at one end to said at least one tape reel and to the magnetic tape at the second end, said leader tape being transparent to the light emitted from said light source; means defining a light transmission aperture in the housing defined by said upper and lower halves when connected; means defining a window in one of said upper and lower halves through which said tape reel can be seen; a structure for attenuating light which does not come directly through said leader tape from said light source and which tends to pass through said light transmission aperture toward said sensor, said structure comprising: a light polarizing element which is disposed in said light transmission aperture, said polarizing element being arranged to transmit light which passes along a line interconnecting the light source and said light transmission aperture.

A further aspect of the invention comes in the form of a system which features a light source; first and second sensors responsive to the light emitted from said light source; means for receiving a cassette in a manner wherein said first and second sensors proximate first and second sides of said cassette, said cassette comprising: first and second halves which when connected together define a cassette housing; first and second tape reels rotatably disposed in said cassette housing; means for defining a structure in said cassette housing which can selectively receive said light source, said structure being defined in a position essentially equidistant from the sides of said cassette housing; means defining first and second light transmission apertures in said cassette housing which juxtapose said first and second sensors, said first and second light transmission apertures being located so that light from said light source can pass through said light transmission apertures to said first and second sensors; an opaque tape wound on said first and second tape reels; first and second leader tape sections, said first and second leader tape sections being connected to each end of said opaque tape and arranged to interconnect the ends of the opaque tape to the tape reels; first and second structures which are one of (a) formed integrally with the cassette housing proximate said first and second light transmission apertures respectively and (b) disposed in said first and second light transmission apertures, said first and second structures attenuating light which does not come directly through said first and second leader tapes from said light source and which tends to pass through said light transmission aperture toward said sensor.

BRIEF DESCRIPTION OF THE DRAWINGS

The various features, merits and advantages of the embodiments of the present invention will become more clearly appreciated as a disclosure of the same is made in conjuction with the appended drawings in which.

DETAILED DESCRIPTION OF THE PREFERRED EMBODIMENTS

Figure 1:
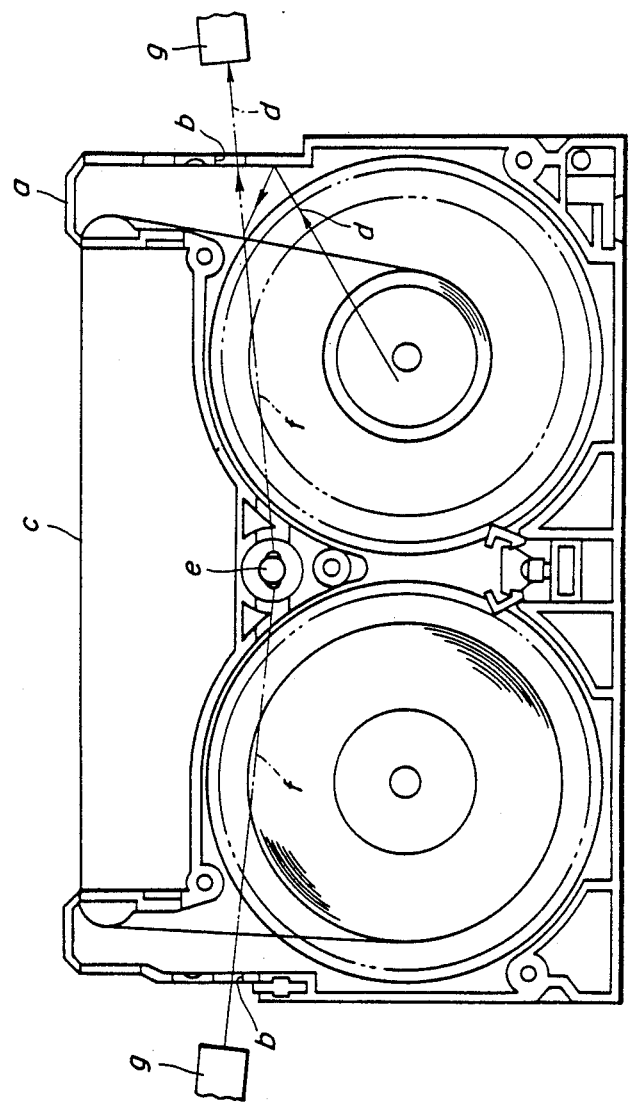
FIG. 1 is a plan view of the lower half of the prior art magnetic tape cassette discussed in the opening paragraphs of the instant disclosure.
Figure 2:
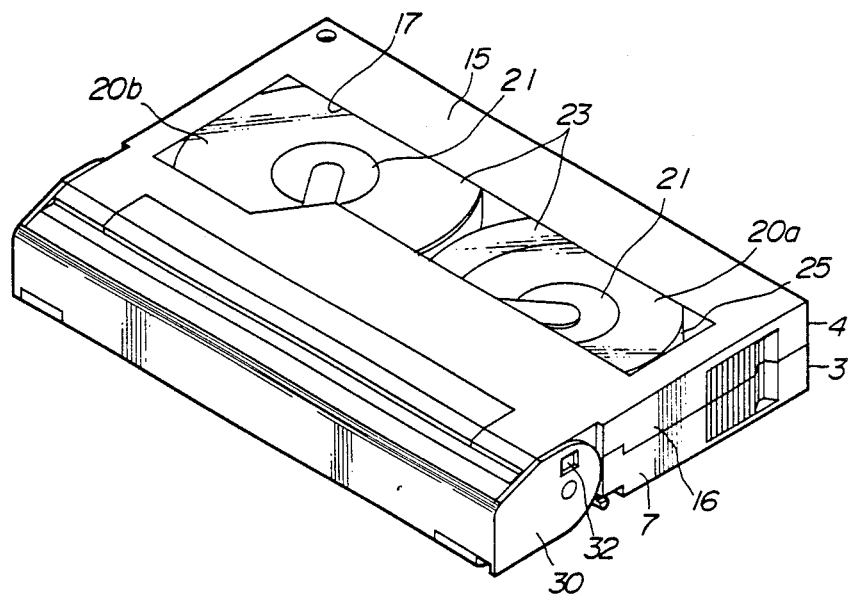
FIG. 2 is a perspective view showing a fully assembled cassette to which the embodiments of the present invention are applicable.
Figure 3:
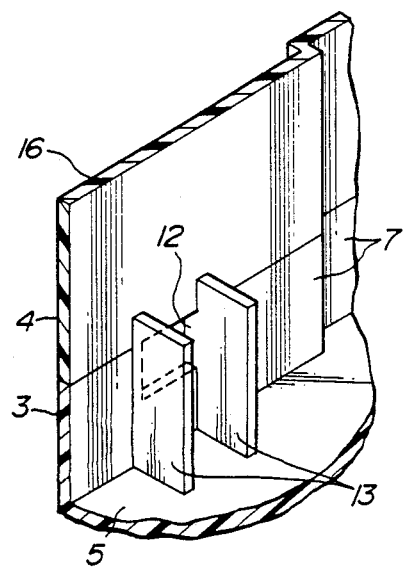
FIG. 3 is a perspective cut-away view of a construction which characterizes a first embodiment of the present invention.

FIGS. 2 to 7 show a first embodiment of the present invention.

As will be appreciated, this cassette is (merely by way of example) of the type suited for use in video recording and reproducing apparatus and includes upper and lower halves 4 and 3. A pivotal cover 30 is connected to the assembled upper and lower halves, and a spring arrangement generally denoted by the numeral 34 (FIG. 6) is arranged to bias the cover toward a closed position.

THE LOWER HALF

The lower half 3 includes a lower major surface 5 (see FIGS. 3 and 4 for example) and is configured to define a recess section 6 which facilitates the drawing of the magnetic tape out of the cassette and its subsequent operative disposition with read/recording heads (not shown). An inwardly depending flange 7 is formed about the entire periphery of the lower half 3. This flange 7 cooperates with a corresponding member on the upper half 4 in a manner to define the outer wall of the cassette when the two halves are assembled together.

The lower half 3 is further formed with two projections 8, 8' at the forward left and right corners thereof. These projections include convex projections (no numerals) over which the tape is arranged to slide and apertures in the ends thereof through which the magnetic tape passes (see FIG. 4). A plurality of bosses 9 are formed as shown. These are formed with screw holes 9a.

Figure 13:
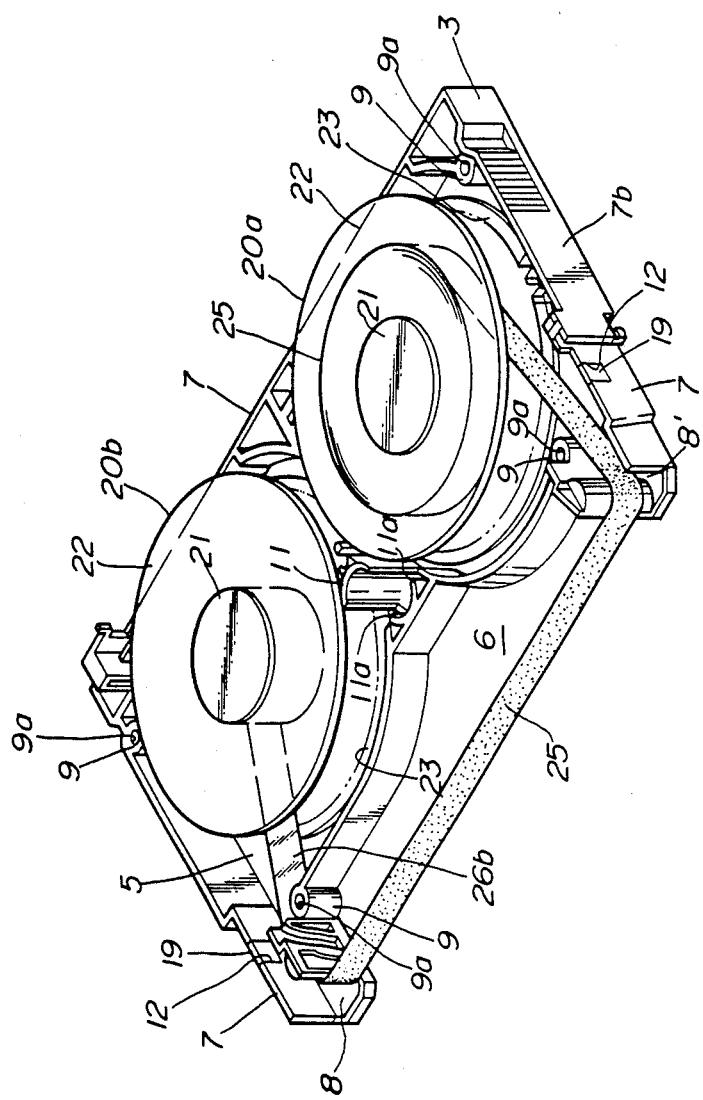
FIG. 13 is a perspective view of a cassette according to the third embodiment wherein the top half has been removed.
Figure 14:
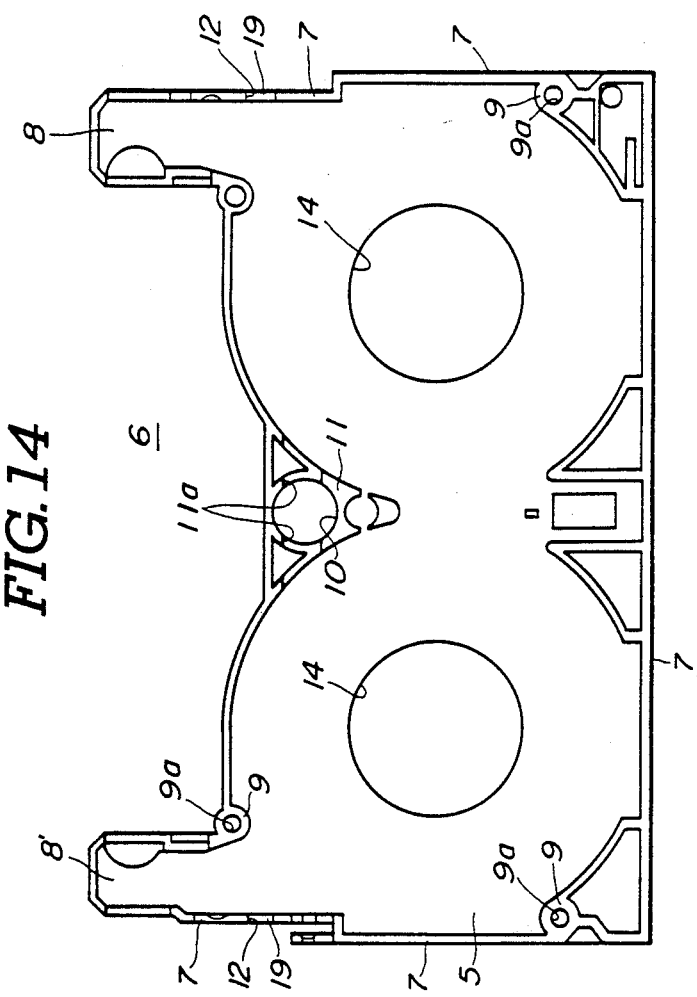
FIG. 14 is a plan view showing the lower half of the cassette shown in FIG. 13.
Figure 15:
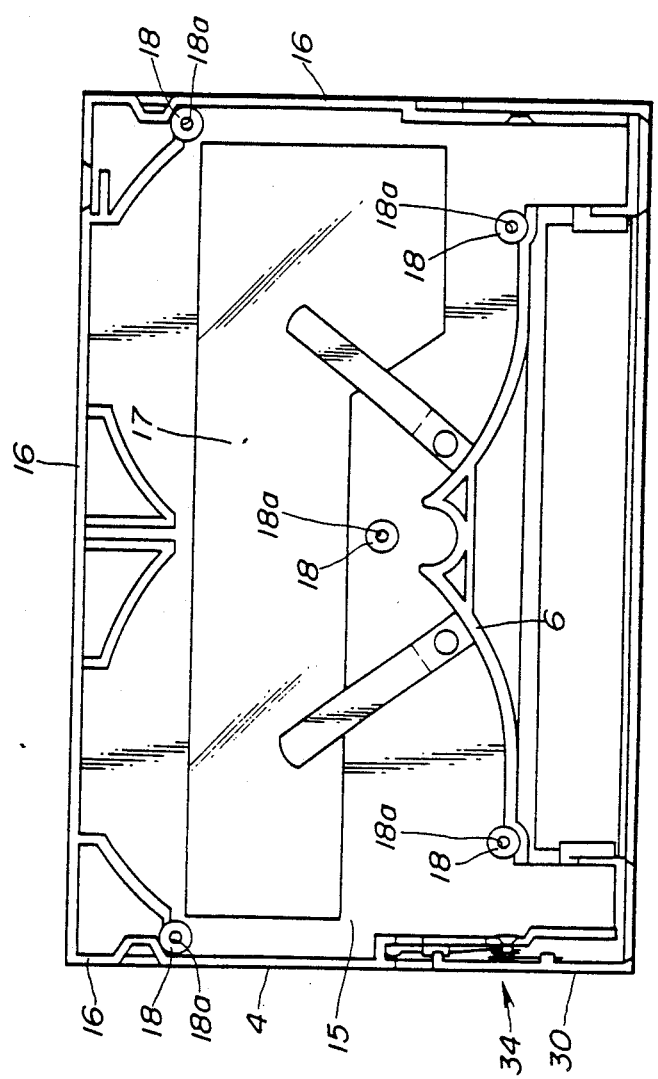
FIG 15 is a plan view of the underside of the top half of the cassette used in the third embodiment.

An aperture 10 for receiving a light source is formed at the front of the lower half 2 at a location essentially mid-way between the projections 8, 8'. Cut-outs 11a, 11a are formed in the wall portion 11 which defines the aperture (see the perspective view of the same in FIG. 13). These cut-outs permit two beams of light to be emitted from the light source toward cut-out sections 12 formed in the inwardly depending flange 7. When the two halves 3, 4 are assembled together the cut-outs 12 define light transmission apertures in the manner illustrated in FIG. 3. These apertures are arranged to cooperate with corresponding apertures 32 (see FIG. 2) formed in the cover 30. With this arrangement when the cover is moved to an operative position, the apertures become aligned so that light can be readily transmitted to the sensors provided in the deck.

In this embodiment inwardly extending baffle-like shield walls 13 are formed to extend inwardly from each side of the light transmission aperture. The function of these walls will be described in more detail hereinlater.

Figure 5:
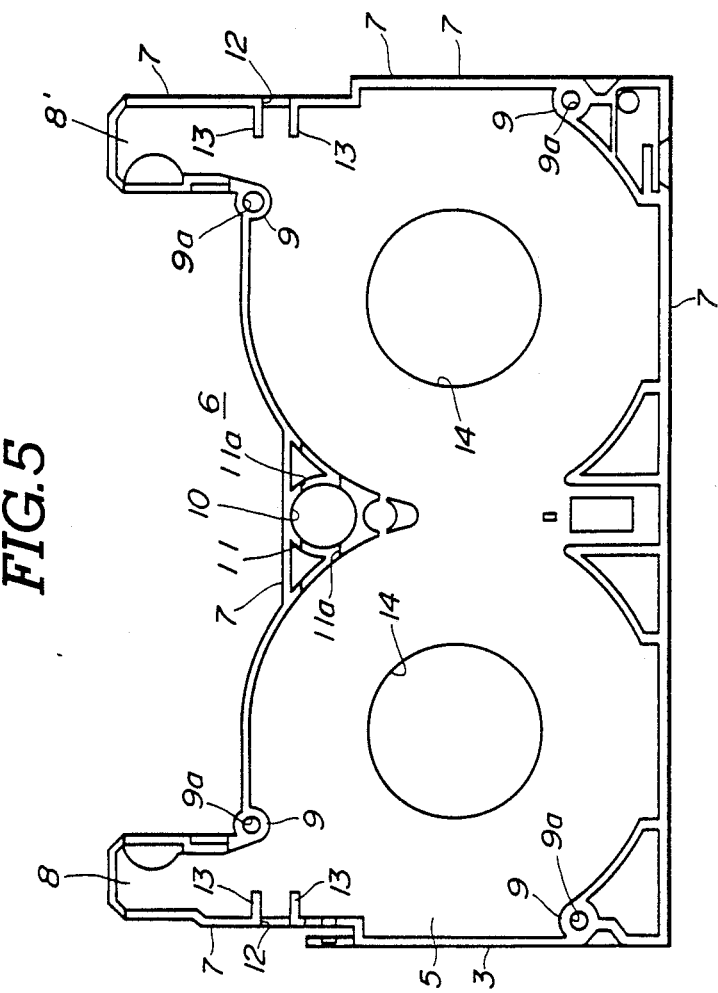
FIG. 5 is a plan view of the arrangement shown in FIG. 4 wherein the tape reels and other elements of the cassette mechanism have been removed.

As shown in FIG. 5, the lower major surface 5 is formed with two relatively large diameter openings 14. These openings are formed on either side of the center of the cassette for reasons which will become apparent hereinlater.

THE UPPER HALF

Figure 6:
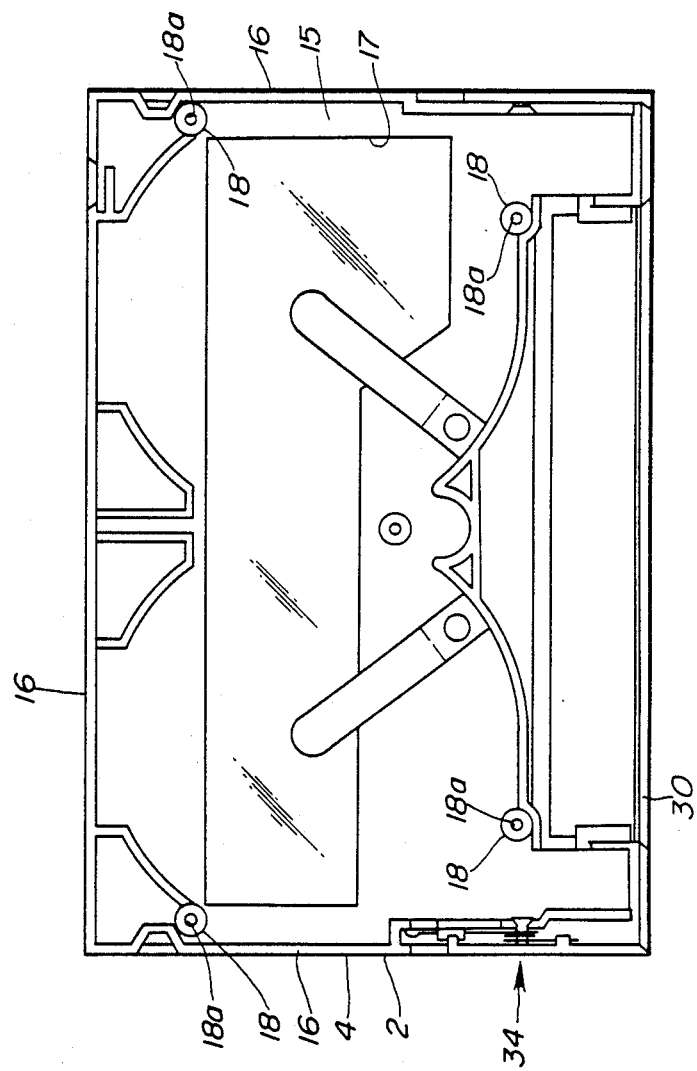
FIG. 6 is a plan view showing the underside of the top half of the cassette to which the first embodiment is applied.

The upper half 4 is formed with an upper major surface 15 and an inwardly depending flange 16. This flange 16 cooperates with the flange 7 formed on the lower half 3 to define the sides of the cassette. As best seen in FIG. 6 the upper half is formed with an elongate window 17 formed of a transparent plastic or the like material. This window 17 serves to permit visual ascertainment of the amount of tape which is wound on each reel and thus permit decisions as to need to rewind, wind forward, use for recording or not, etc.

The upper half is further formed with bosses 18 in which screw holes 18a are formed. These bosses mate with the bosses formed 9 in the lower half when the cassette is assembled in a manner that the screw holes 9a and 18a are aligned.

TAPE REELS

Tape reels 20a and 20b are rotatably disposed in the cassette. These reels include integrally formed hubs 21, and upper and lower flanges 22, 23. The upper flanges 22 are arranged to be transparent so that the amount of magnetic tape which is wound on each of the reels is visible through the window 17. In order to permit the reels to be driven, the hub is formed with a suitable axial blind bore 24 into which lugs can be selectively inserted via the openings 14 formed in the lower major surface 5 of the lower half 3.

MAGNETIC TAPE

In the drawings, the numeral 25 denotes a length of magnetic tape. This tape 25 has transparent portions or so called leader tapes 26a, 26b at each end thereof. The free ends of these transparent portions are connected to a respective reel hub 21.

For the sake of explanation the left hand reel will be referred to hereinafter as the S reel while the right hand reel will be referred to as the T reel. Thus, as shown in FIG. 4 the magnetic tape 25 is arranged to extend from the S reel, pass out through the left hand extension 8, extend across the recess 6, pass in through the aperture formed in the right hand extension 8' and terminate at the hub of the T reel.

Figure 4:
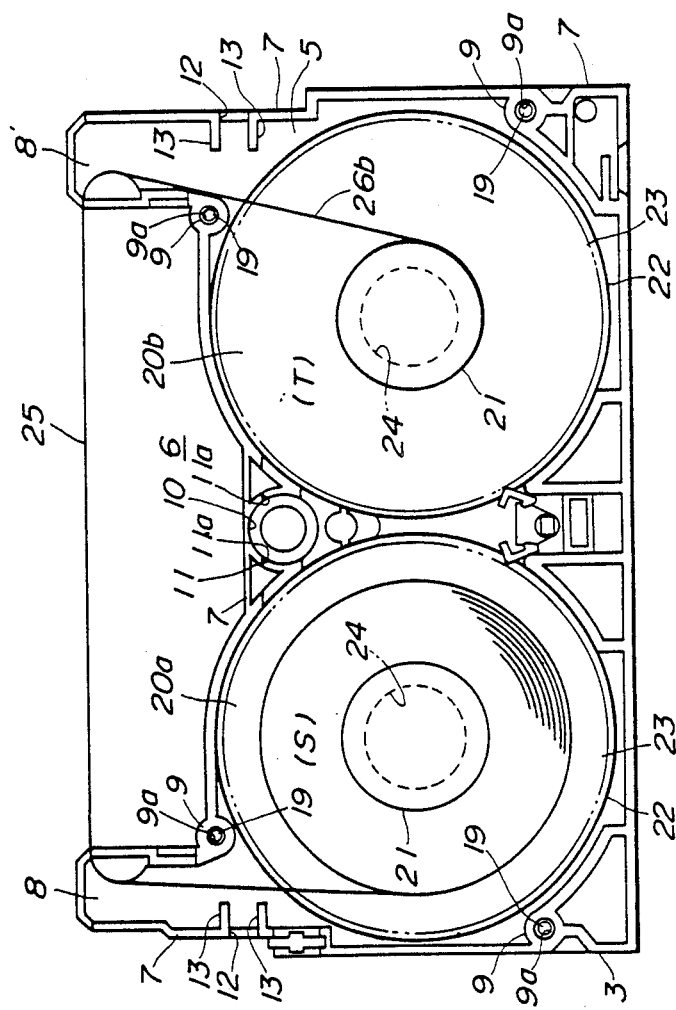
FIG. 4 is a plan view of a lower half of a cassette which includes a construction according to the first embodiment of the present invention.

It will be noted from FIG. 4 that the magnetic tape extends between the cut outs 11a and the diametrically opposed light transmission apertures defined by the recesses 12 and therefore blocks light transmission therebetween until one of the transparent leader tapes 26a, 26b begins to unwind from a reel.

OPERATION

With the above disclosed arrangement when the cassette is loaded into a deck, the deck mechanism picks up the tape and draws it into position. As this portion of the operation is well known in the art of video decks and has no particular bearing on the present invention no further disclosure will be given for brevity.

It will be noted that in the deck to which the present invention is applicable the cassette is fitted with a light source 27 and light sensors 28a and 28b.

Figure 7:
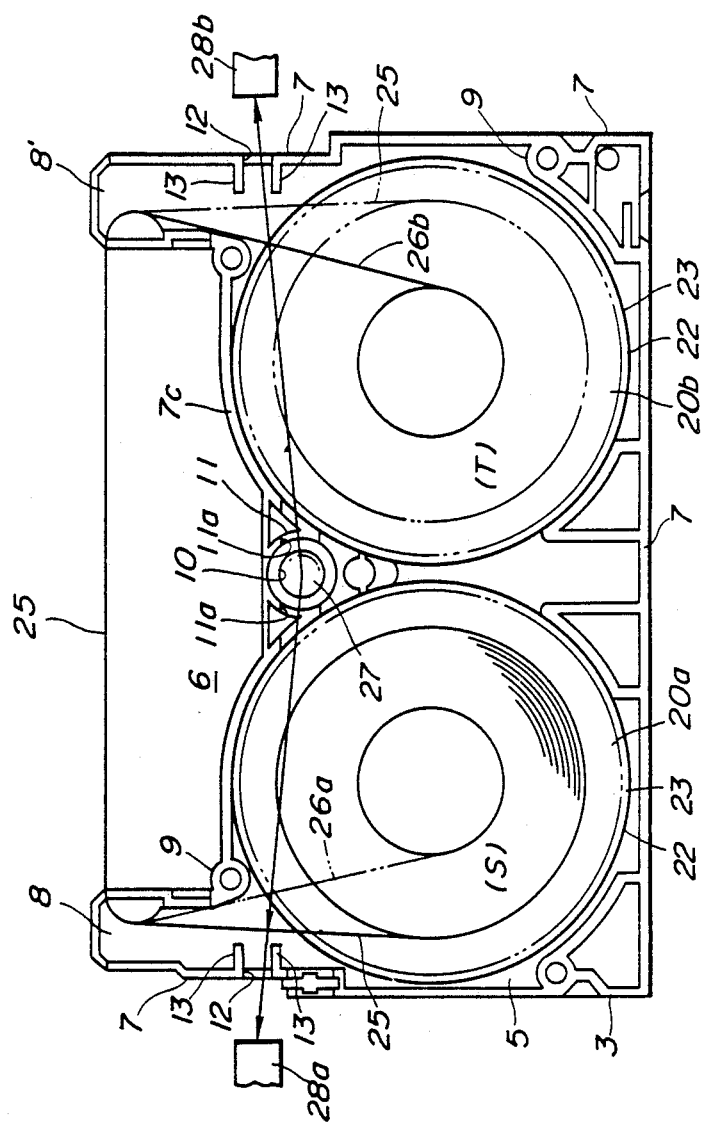
FIG. 7 is a plan view similar to FIG. 4 showing the operational characteristics of the first embodiment.
Figure 8:
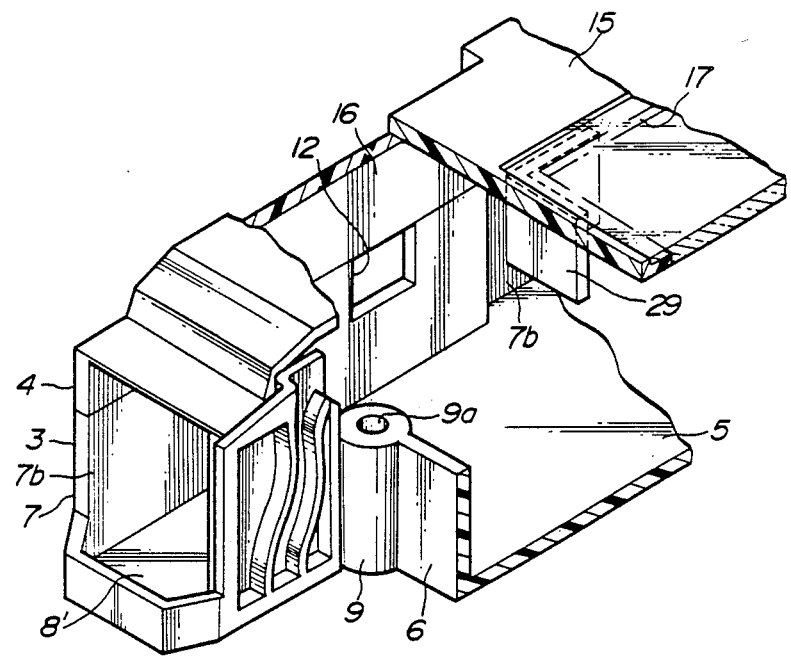
FIG. 8 is a perspective cut-away view of a construction which characterizes a second embodiment of the present invention.
Figure 9:
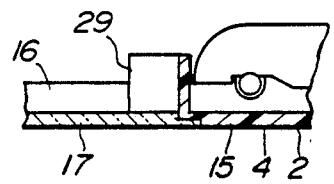
FIG. 9 is sectional elevation of the arrangement shown in FIG. 8 as taken along section line of FIG. 11.
Figure 10:
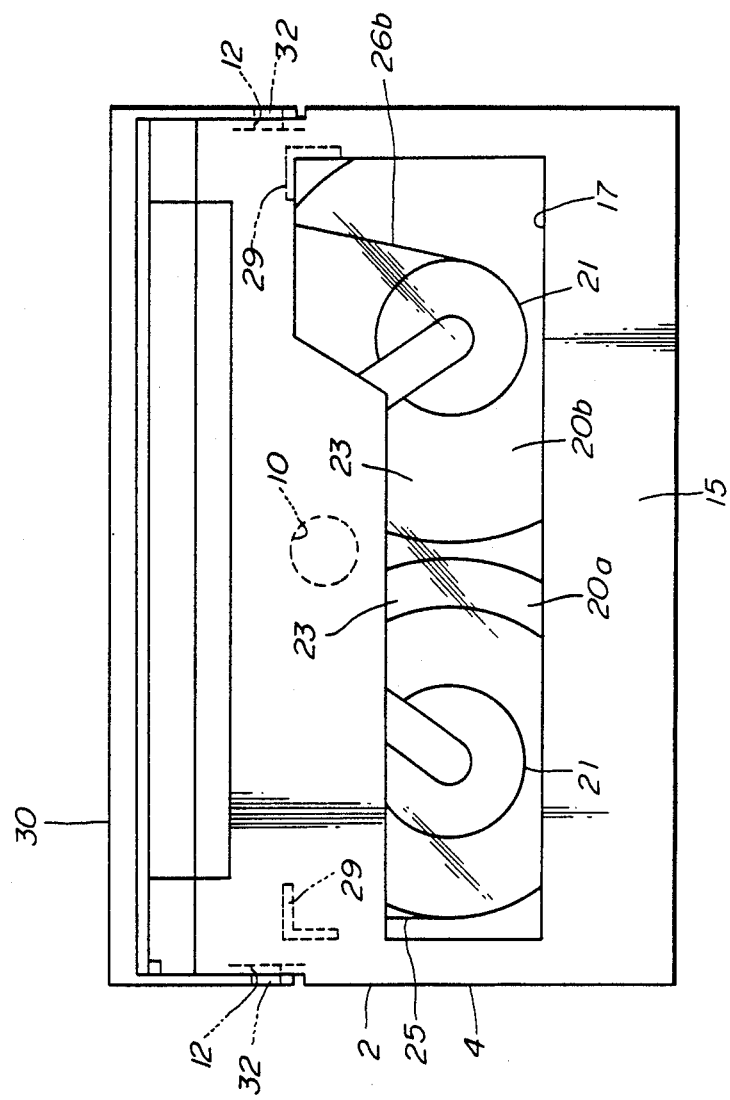
FIG. 10 is a plan view of a fully assembled cassette according to the second embodiment of the present invention.

When the cassette is loaded into the deck the light source 27 is inserted into the aperture 10 in the manner shown in FIG. 7. In the illustrated arrangement the take up reel - reel T is unwound (solid line) to the point that the leader tape 26b extends between the light source and the sensor 28b. Under these conditions light is permitted to pass from the light source to the sensor. However, on the other hand as the magnetic tape 25 (solid line) extends between the light source 27 and the sensor 28a, the transmission of the light beam from the light source to that sensor is blocked.

When the tape is driven in the forward direction such as occurs when running a video movie or the like, the tape winds off reel S onto reel T until such time as the tape assumes the condition shown in two dot phantom. Under these conditions, the second of the leader tapes begins to unwind off reel S and thus permit light from the light source to reach sensor 28a while on the other side the opaque magnetic tape blocks light transmission to the sensor 28b.

With this embodiment the provision of the shield walls 13 prevents the passage of reflected light rays to the sensors 28a, 28b and permits only the direct beam from the light source 27 to pass through the light transmission apertures when a leader tape extends between one of the sensors and the light source 27.

Thus, even though light may infiltrate into the interior of the cassette through the window 17 for example, the walls 13 screen out any beams that may result from the same and obviate any stoppage or the like undesired operation due to a false tape end detection signal being generated by one of the two light sensors 28a, 28b.

Further, as will be readily apparent, the shield walls 13 can easily be moulded simultaneously with the rest of the lower half 3 and thus totally eliminates the troublesome assembly problems encountered with the prior art.

SECOND EMBODIMENT

Figure 11:
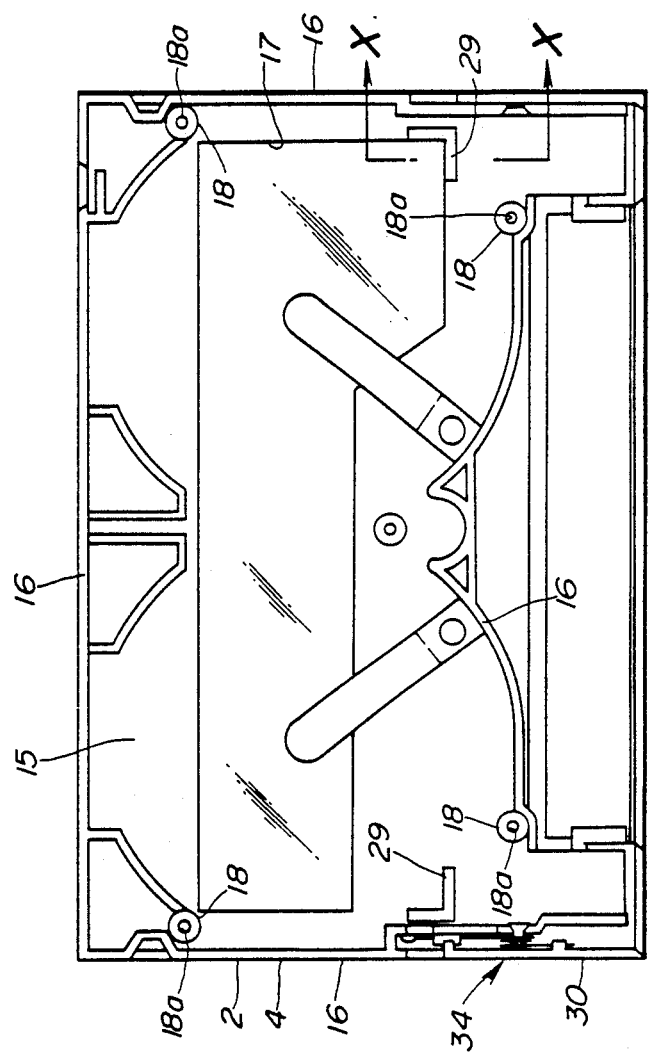
FIG. 11 is a plan view showing the underside of the top half of the cassette according to the second embodiment of the present invention.
Figure 12:
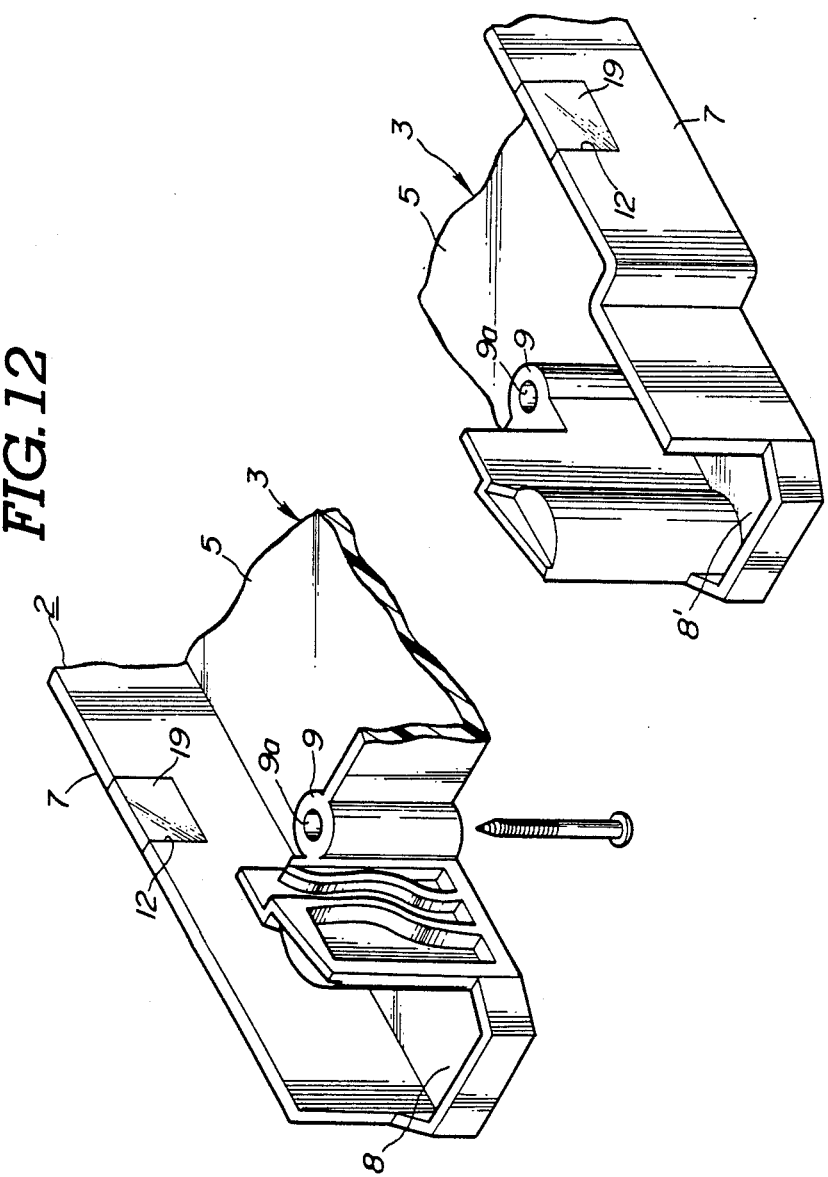
FIG. 12 is a perspective cut-away view showing the construction which characterizes a third embodiment of the present invention.

FIGS. 8 to 11 show a second embodiment of the present invention. In this arrangement the shield walls which block out the error inducing light rays are essentially L-shaped and formed on the upper half 4. As best seen in FIG. 11 one of the walls is formed at the corners of the window section 17 most proximate the recess 12 formed in the right hand side (see FIG. 10) of the cassette.

With this provision any light that tends to enter the interior of the cassette through the window is prevented from propergating toward this recess 12 which defines the light transmission aperture on that side of the arrangement. A second corresponding wall 29 is formed in a corresponding position of the upper half. However, as will be apparent from FIG. 10 this wall is somewhat removed from the window on that side of the cassette. Nevertheless, its position proximate the left hand side recess 12 provides desirable shielding from any stray rays of light that may have entered the interior of the arrangement.

In this instance also the shield walls 29 can be formed integrally with the rest of the upper half 4 and thus obviate the problems encountered with the prior art.

It is possible to use the first and second embodiments in combination if so desired with essentially no increase in manufacturing cost.

THIRD EMBODIMENT

Figure 16:
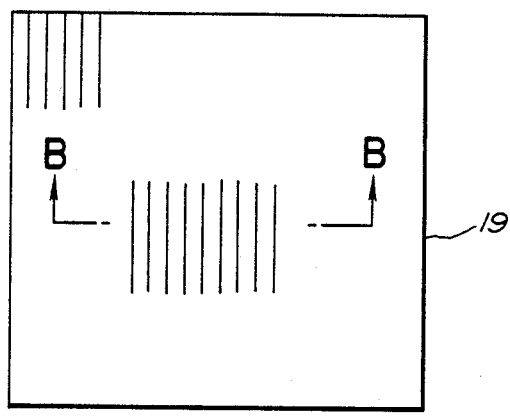
FIG. 16 is an elevational view of the transparent light polarizing element which forms a vital part of the third embodiment.
Figure 17:
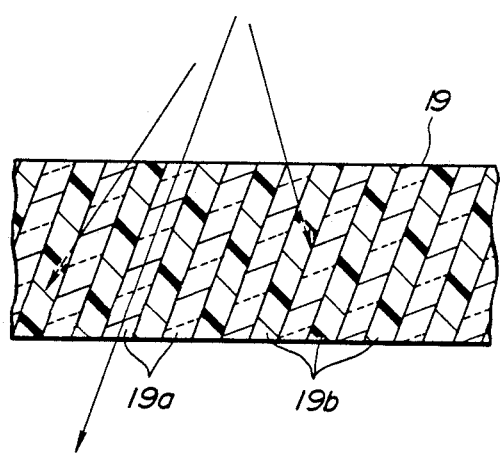
FIG. 17 is a sectional view as taken along section line B—B of FIG. 16.

FIGS. 12 to 18 show a third embodiment of the present invention. In this arrangement a light polarizing element 19 is disposed in the recess 12 defining the light transmission aperture. This element can be selected of any known type of polarizing material. However, in this instance, by way of example, the elements is formed so as to comprise alternate layers of material 19a and 19b which are respectively transparent and opaque to the light. Accordingly, as shown in FIGS. 16 and 17 only light rays having a predetermined orientation may pass through the element 19 without impinging on the opaque layers 19b. As will be readily understood, after impingement on a non-transparent layer the light is diffused to the point where transmission thereof is essentially non-existent and erroneous tape end detection signals cannot be triggered.

Figure 18:
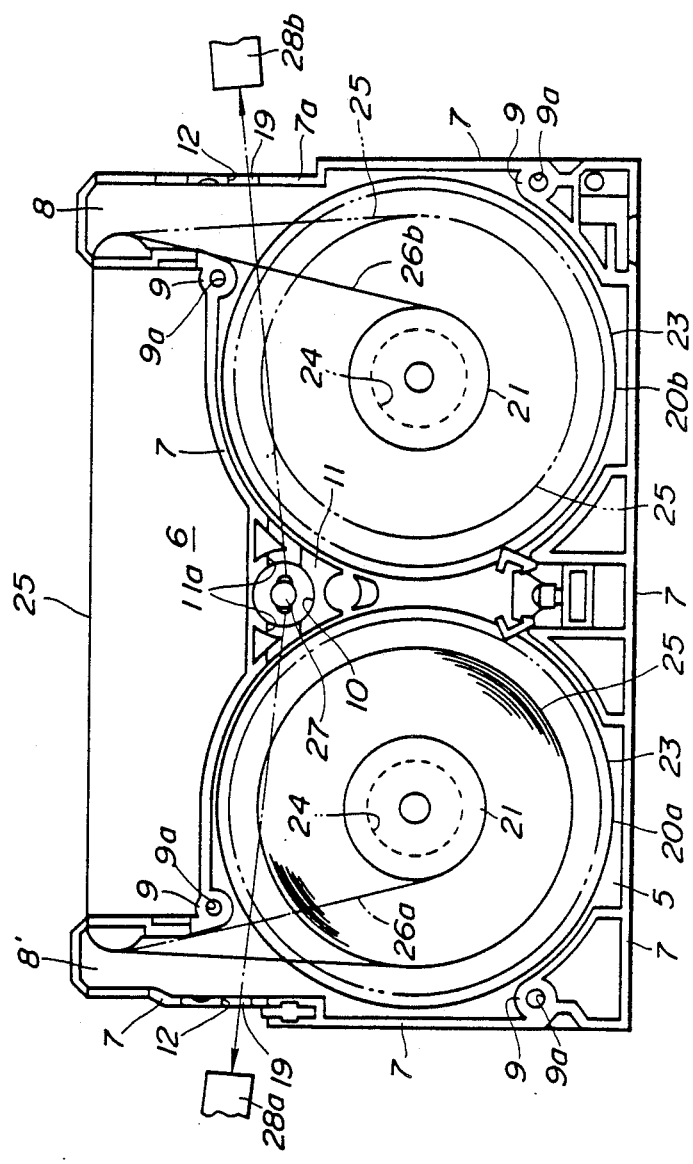
FIG. 18 is a plan view showing the operation of the third embodiment.

The operation of this embodiment is deemed to be adequately clear from the drawings, for example FIG. 18 wherein the location of the light polarizing elements with respect to the light source is clearly depicted. It is further clear from this figure that the light from the light source impinges on the surface of the polarizing elements at a slight angle.

For this reason, the light polarizing elements 19 are produced in manner wherein the layers of the transparent and opaque materials 19a and 19b are slightly angled in accordance with the angle at which the light from the light source 27 tends to propagate toward the cut-out 12.

With this arrangement it is possible to arrange the light polarizing element 19 so that, as shown in FIG. 18, only the light which is transmitted directly from the light source 27 is able to pass through to the sensors 28a, 28b and impinge on the same in a manner which triggers a tape end signal.

It is further possible to, if so desired, polarize the light emitted from the light source 27 and arrange for the polarizing elements to be aligned in a manner that the polarized light from the light source will pass therethrough while reflected light which becomes polarized by the reflection is apt to be polarized in a direction different from that of the elements 19 and will be screened out.

This embodiment alone produces remarkably good results. However, it is further possible to combine the same with either one or both of first and second embodiments if so desired.

FOURTH EMBODIMENT

Figure 19:
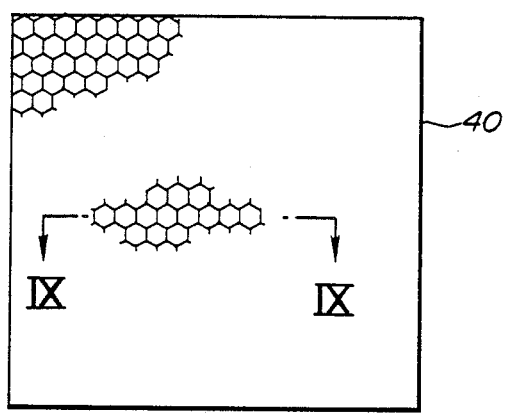
FIG. 19 is an elevational view of a transparent light polarizing element according to a fourth embodiment of the present invention.
Figure 20:
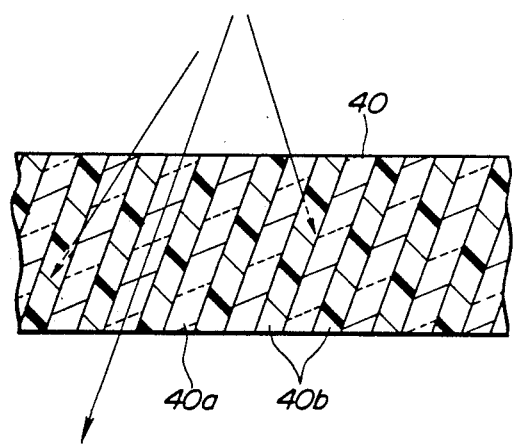
FIG. 20 is a sectional view as taken along section line IX—IX of FIG. 19.

FIGS. 19 and 20 show a fourth embodiment of the present invention. This arrangement is essentially the same as that of the third embodiment except that the light polarizing element 19 is replaced with an element 40 which as best seen in FIG. 20 is comprised of alternative columns 40a, 40b of transparent and opaque material which are formed together to define a honeycomb-like structure. The function of this element is illustrated in FIG. 20. As is shown, beams of light which are not aligned with the direction in which transparent columns 40a extend, they tend to impinge on the surfaces of the opaque ones and become attenuated to the level of having no effect on the sensor located outside the cassette.

FIFTH EMBODIMENT

Figure 21:
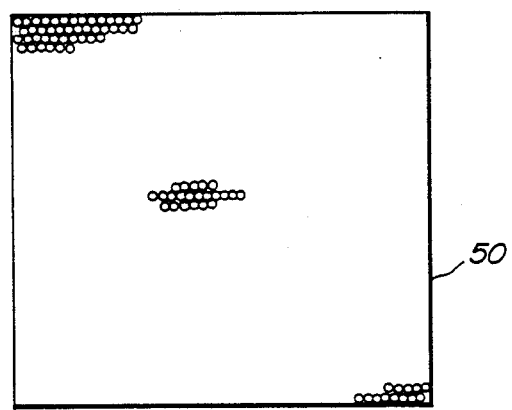
FIGS. 21 and 22 are respectively elevation and perspective views showing the transparent light polarizing element which is used in a fifth embodiment of the present invention.
Figure 22:
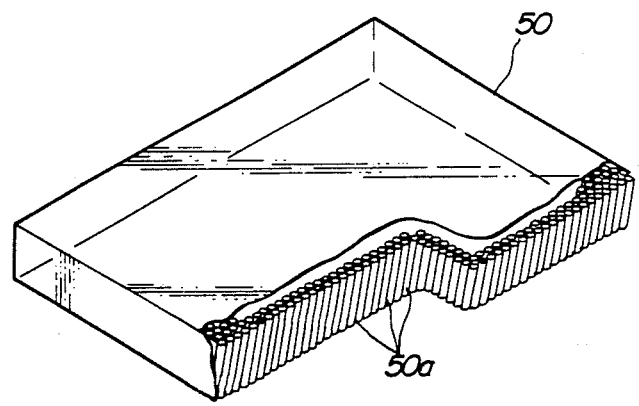
Figure 23:
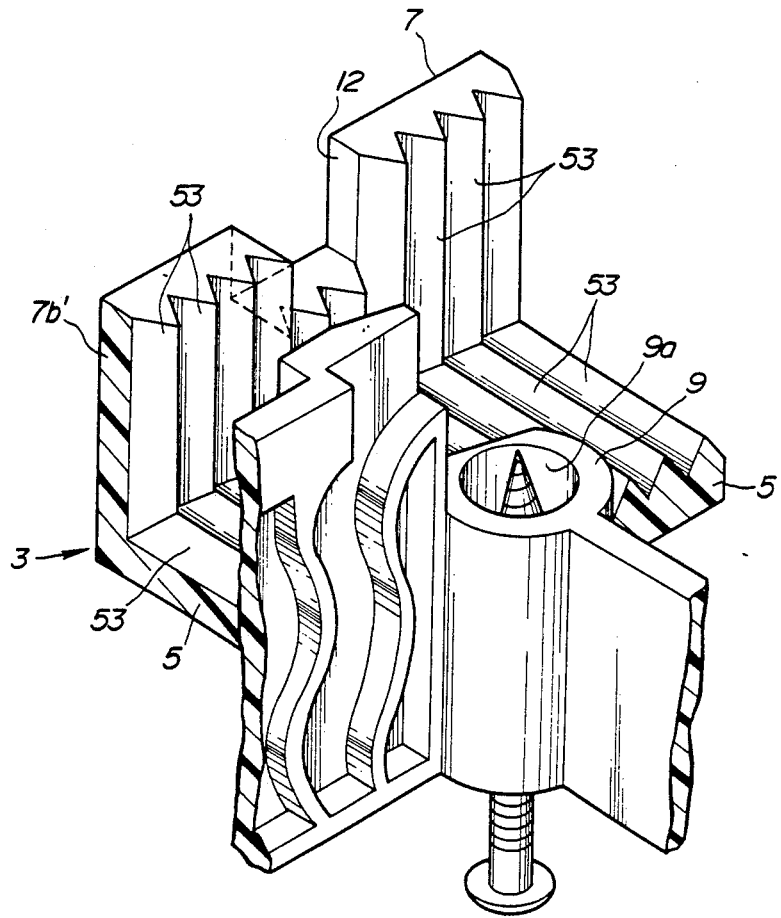
FIG. 23 is a cut-away perspective view showing the construction which characterizes a sixth embodiment of the present invention.
Figure 24:
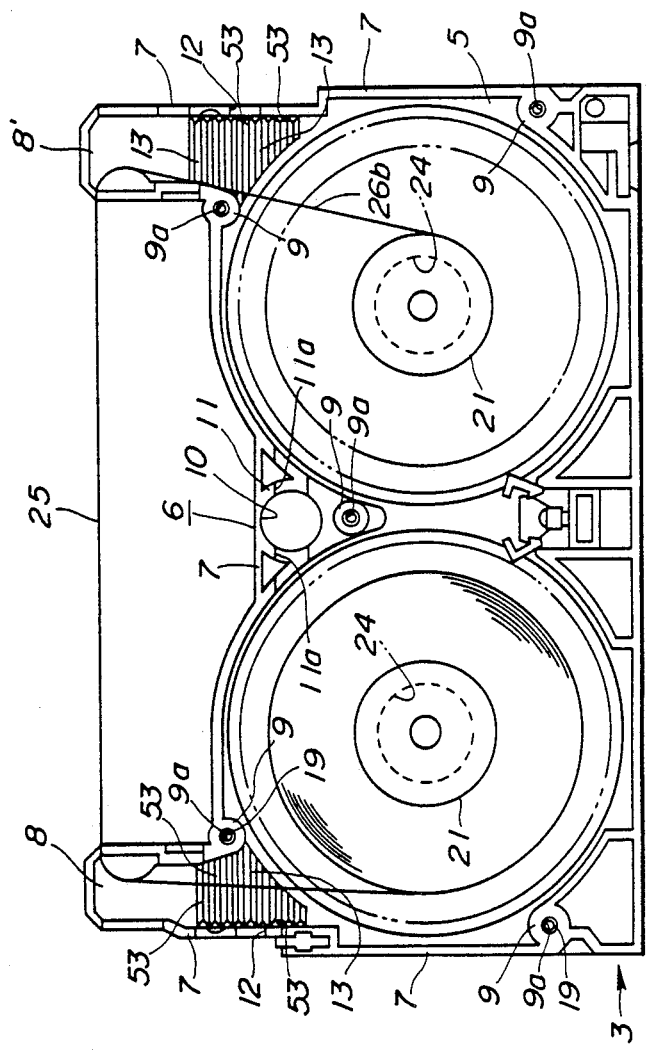
FIG. 24 is a plan view showing the lower half of the cassette according to the sixth embodiment.
Figure 25:
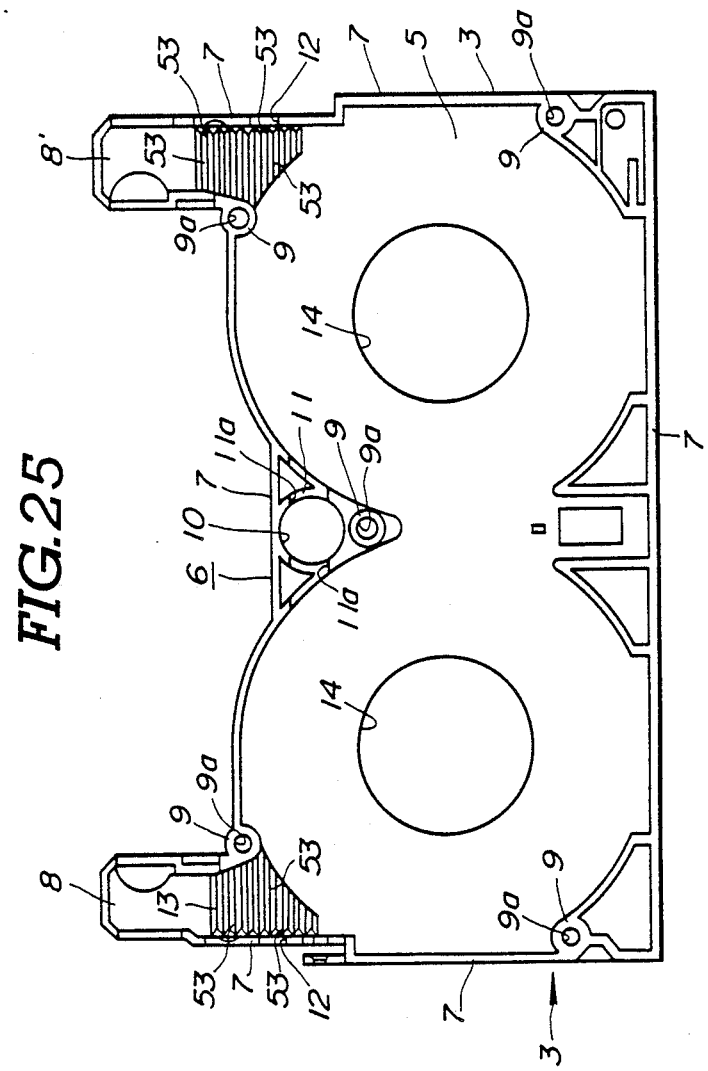
FIG. 25 is a plan view similar to that shown in FIG. 24 wherein reels and other elements have been removed for clarity.
Figure 26:
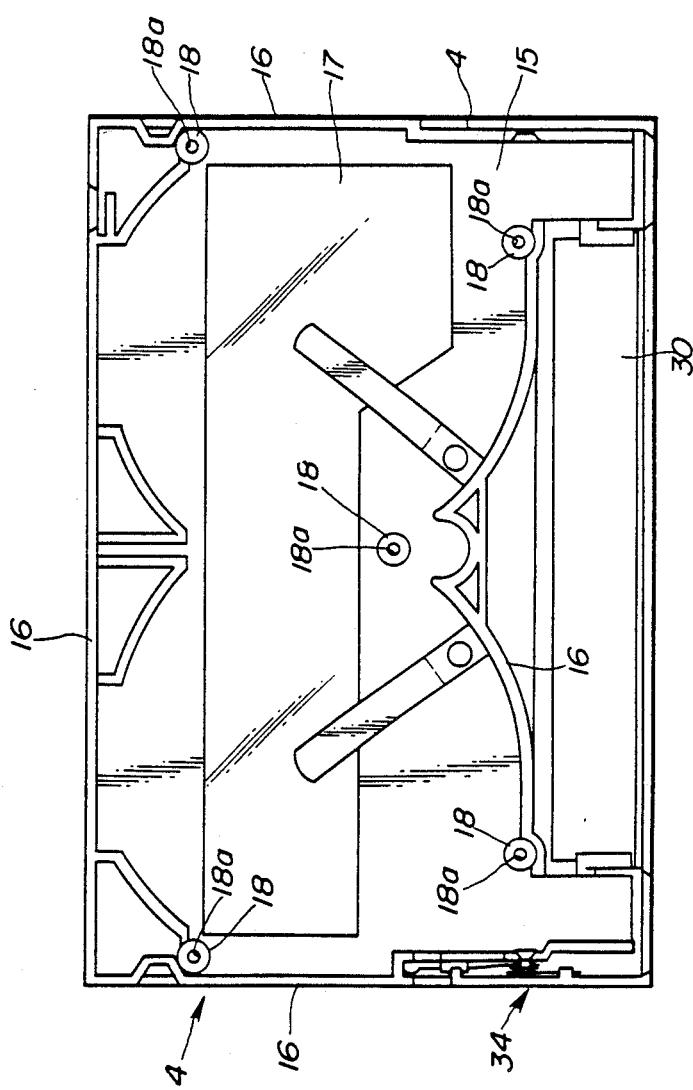
FIG. 26 is a plan view showing the underside of the top half of the cassette according the sixth embodiment.
Figure 27:
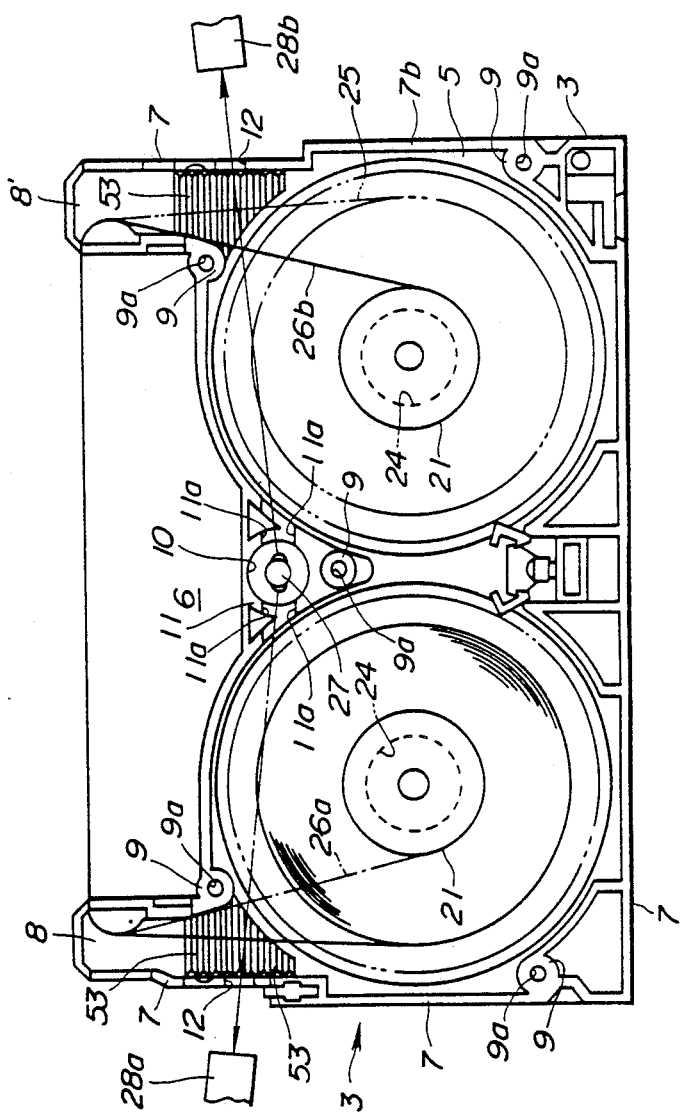
FIG. 27 is a plan view showing the sixth embodiment in operation.

FIGS. 21 and 22 show a fifth embodiment of the present invention. In this embodiment the polarizing element 50 which is disposed in the cut-outs 12 which define the light transmission aparture, is formed of a large number of optical fibers 50a which are packed snugly together in a manner which excludes any gaps therebetween. Although this arrangement does not include any opaque members, the interfaces defined between the fibers 50a tends to produce the same effect as illustrated in FIGS. 17 and 20. Accordingly, redundant explanation of the operation of this embodiment will be omitted for brevity.

SIXTH EMBODIMENT

FIGS. 23 to 27 show a sixth embodiment of the present invention. In this arrangement the interior of the lower half 3 of the cassette is formed with a plurality of corrugations 53 in the areas in which the the cut-outs 12 are formed. In this instance the corrugations 53 are formed both on the lower major surface 5 and the upwardly extending flange 7 as shown. The corrugations have a saw-tooth profile wherein each of the same has an essentially triangular cross-section.

This construction serves to reflect and redirect any stray beams of light that may have entered the cassette, particularly through the large transparent window 17 and/or been reflected within the cassette (such as off the flanges of the tape reels), in a manner which scatters and/or diffuses the beams of and reduces transmissions which might tend to escape through the cut-outs 12 and impinge on the sensors 28a, 28b and thus obviates the possibility of an improper tape end detection.

As the operation of the instant embodiment will be clearly understood by those skilled in the art when familiar with the operation of the first and second embodiments (by way of example) redundant explanation of the same will be omitted.

In this instance the corrugations 53 are shown formed on the lower half 3 of the cassette However, the present invention is not limited to this provision and corresponding corrugations can be formed on the upper half 4 or in different locations in addition to those in the lower one if so desired.

As will be readily understood the corrugations which characterize the instant embodiment can be formed during the formation of the lower (and/or upper) half of the cassette and thus obviate the cost incurring constructions which plague the prior art.

It is possible to combine the instant embodiment with any of the previously disclosed arrangements if deemed either necessary or appropriate.

Although the above disclosure has been made in conjunction with cassettes of the nature used in VTR equipment, the present invention is not limited thereto and can find advantageous application in other forms of cassettes, particularly in the smaller types (e.g. short VTR cassettes, music and/or data recording and the like) wherein space is at a premium and wherein accurately sensing the end of a tape being approached is useful in avoiding tape breakage, stretching and/or the like damage.

What is claimed is:

1. In a tape cassette including a tape having at least one tape end having greater light transmittance than the rest of the tape, the combination of:
   means for housing a light source;
   means defining a light transmission aperture in a wall portion of the cassette; and
   means for sensing the tape end being reached, said tape end sensing means comprising means associated with said light transmission aperture for preventing light which does not come directly from the light source from passing through said light transmission aperture, said light passage preventing means being formed integrally with the cassette housing.

2. A tape cassette as claimed in claim 1 wherein said light passage preventing means comprises a wall portion formed integrally with the cassette proximate said light transmission aperture.

3. A tape cassette as claimed in claim 1 wherein said light passage preventing means comprises two wall portions formed integrally with the cassette in close proximity to and on either side of said light transmission aperture.

4. In a tape cassette
   means for housing a light source;
   means defining a light transmission aperture in a wall portion of the cassette;
   means associated with said light transmission aperture for preventing light which does not come directly from the light source from passing through said light transmission aperture, said light passage preventing means comprising a light polarizing element disposed in said light transmission aperture.

5. In a tape cassette
   means for housing a light source;
   means defining a light transmission aperture in a wall portion of the cassette;
   means associated with said light transmission aperture for preventing light which does not come directly from the light source from passing through said light transmission aperture, said light passage preventing means comprising a plurality of corrugations formed on an interior surface of the cassette in close proximity of said light transmission aperture.

6. In a tape cassette
   means for housing a light source;
   means defining a light transmission aperture in a wall portion of the cassette;
   a tape reel on which a tape is wound, said tape having a section which is transparent to the light emitted from said light source;

means associated with said light transmission aperture for attenuating light which does not come directly from the light source and pass through said transparent section in a manner that it does not pass through said light transmission aperture and reach a sensor disposed outside of the cassette in a manner which triggers the sensor to produce a signal, said light attenuating means being formed integrally with the cassette.

7. A tape cassette as claimed in claim 6 wherein said light attenuating means comprises a wall portion formed integrally with the cassette proximate said light transmission aperture.

8. A tape cassette as claimed in claim 6 wherein said light attenuating means comprises two wall portions formed integrally with the cassette in close proximity to and on either side of said light transmission aperture.

9. In a tape cassette
means for housing a light source;
means defining a light transmission aperture in a wall portion of the cassette;
a tape reel on which a tape is wound, said tape having a section which is transparent to the light emitted from said light source;
means associated with said light transmission aperture for attenuating light which does not come directly from the light source and pass through said transparent section in a manner that it does not pass through said light transmission aperture and reach a sensor disposed outside of the cassette in a manner which triggers the sensor to produce a signal, said light attenuating means comprising a light polarizing element disposed in said light transmission aperture.

10. In a tape cassette
means for housing a light source;
means defining a light transmission aperture in a wall portion of the cassette;
a tape reel on which a tape is wound, said tape having a section which is transparent to the light emitted from said light source;
means associated with said light transmission aperture for attenuating light which does not come directly from the light source and pass through said transparent section in a manner that it does not pass through said light transmission aperture and reach a sensor disposed outside of the cassette in manner which triggers the sensor to produce a signal, said light attenuating means comprising a plurality of corrugations formed on an interior surface of the cassette in close proximity of said light transmission aperture.

11. A cassette for use in a device which is equipped with a light source and a sensor responsive to the light emitted from said light source, said cassette comprising:
a first half;
a second half said second half being connectable to said first half in a manner to define a housing, one of said upper and lower halves being formed with a structure into which said light source can be selectively introduced;
at least one tape reel disposed in said housing;
magnetic tape wound on said at least one tape reel;
a leader tape connected at one end to said at least one tape reel and to the magnetic tape at the second end, said leader tape being transparent to the light emitted from said light source;
means defining a light transmission aperture in the housing defined said upper and lower halves when connected;
a structure for attenuating light which does not come directly through said leader tape from said light source and which tends to pass through said light transmission aperture toward said sensor, said structure comprising:
two wall portions which project from opposed sides of said light transmission aperture, said wall portions being formed integrally with one of said upper and lower halves, said wall portions extending essentially in the direction of the structure into which the light source can be selectively introduced.

12. A cassette for use in a device which is equipped with a light source and a sensor responsive to the light emitted from said light source, said cassette comprising:
a first half;
a second half, said second half being connectable to said first half in a manner to define a housing, one of said upper and lower halves being formed with a structure into which said light source can be selectively introduced;
at least one tape reel disposed in said housing;
magnetic tape wound on said at least one tape reel;
a leader tape connected at one end to said at least one tape reel and to the magnetic tape at the second end, said leader tape being transparent to the light emitted from said light source;
means defining a light transmission aperture in the housing defined said upper and lower halves when connected;
means defining a window in one of said upper and lower halves through which said tape reel is visible;
a structure for attenuating light which does not come directly through said leader tape from said light source and which tends to pass through said light transmission aperture toward said sensor, said structure comprising:
a wall portion which is formed integrally with one of said upper and lower halves and which is disposed between said window and said light transmission aperture for preventing the transmission of light which enters the interior of said cassette through said window from propergating toward said light transmission aperture.

13. A cassette for use in a device which is equipped with a light source and a sensor responsive to the light emitted from said light source, said cassette comprising:
a first half;
a second half, said second half being connectable to said first half in a manner to define a housing, one of said upper and lower halves being formed with a structure into which said light source can be selectively introduced;
at least one tape reel disposed in said housing;
magnetic tape wound on said at least one tape reel;
a leader tape connected at one end to said at least one tape reel and to the magnetic tape at the second end, said leader tape being transparent to the light emitted from said light source;
means defining a light transmission aperture in the housing defined said upper and lower halves when connected;

means defining a window in one of said upper and lower halves through which said tape reel can be seen;

a structure for attenuating light which does not come directly through said leader tape from said light source and which tends to pass through said light transmission aperture toward said sensor, said structure comprising:

a light polarizing element which is disposed in said light transmission aperture, said polarizing element being arranged to transmit light which passes along a line interconnecting the light source and said light transmission aperture.

14. In a system a light source;

first and second sensors responsive to the light emitted from said light source;

means for receiving a cassette in manner wherein said first and second sensors proximate first and second sides of said cassette, said cassette comprising:

first and second halves which when connected together define a cassette housing;

first and second tape reels rotatably disposed in said cassette housing;

means for defining a structure in said cassette housing which can selectively receive said light source, said structure being defined in a position essentially equidistant from the sides of said cassette housing;

means defining first and second light transmission apertures in said cassette housing which juxtapose said first and second sensors, said first and second light transmission apertures being located so that light from said light source can pass through said light transmission apertures to said first and second sensors;

an opaque tape wound on said first and second tape reels;

first and second leader tape sections, said first and second leader tape sections being connected to each end of said opaque tape and arranged to interconnect the ends of the opaque tape to the tape reels; and first and second structures which are disposed in said first and second light transmission apertures, said first and second structure attenuating light which does not come directly through said first and second leader tapes from said light source and which tends to pass through said light transmission aperture toward said sensor.

15. In a system a light source;

first and second sensors responsive to the light emitted from said light source;

means for receiving a cassette in a manner wherein said first and second sensors proximate first and second sides of said cassette, said cassette comprising:

first and second halves which when connected together define a cassette housing;

means for defining a structure in said cassette housing which can selectively receive said light source, said structure being defined in a position essentially equidistant from the sides of said cassette housing;

means defining first and second light transmission apertures in said cassette housing which juxtapose said first and second sensors, said first and second light transmission apertures being located so that light from said light source can pass through said light transmission apertures to said first and second sensors;

an opaque tape wound on said first and second tape reels;

first and second leader tape sections, said first and second leader tape sections being connected to each end of said opaque tape and arranged to interconnect the ends of the opaque tape to the tape reels; and first and second structures each comprising two wall portions which are formed integrally with a flange of the second half which defines in part a side wall of the cassette, said wall structures extending essentially parallel with each other from each lateral side of a light transmission aperture and in the direction of the structure in which said light source is selectively receivable.

16. In a system.

a light source;

first and second sensors responsive to the light emitted from said light source;

means for receiving a cassette in a manner wherein said first and second sensors proximate first and second sides of said cassette, said cassette comprising:

first and second halves which when connected together define a cassette housing;

means for defining a structure in said cassette housing which can selectively receive said light source, said structure being defined in a position essentially equidistant from the sides of said cassette housing;

means defining first and second light transmission apertures in said cassette housing which juxtapose said first and second sensors, said first and second light transmission apertures being located so that light from said light source can pass through said light transmission apertures to said first and second sensors;

an opaque tape wound on said first and second tape reels;

first and second leader tape sections, said first and second leader tape sections being connected to each end of said opaque tape and arranged to interconnect the ends of the opaque tape to the tape reels;

means defining a window in the first half, said window permitting said first and second reels to be visible from outside the cassette; and first and second structures each comprising an L-shaped wall portion formed proximate a corner of said window, each L-shaped wall portion being arranged to block rays of light which can enter the cassette via said window and propagate toward said first and second light transmission apertures.

17. In a system a light source;

first and second sensors responsive to the light emitted from said light source;

means for receiving a cassette in a manner wherein said first and second sensors proximate first and second sides of said cassette, said cassette comprising:

first and second halves which when connected together define a cassette housing;

means for defining a structure in said cassette housing which can selectively receive said light source, said structure being defined in a position essentially equidistant from the sides of said cassette housing;

means defining first and second light transmission apertures in said cassette housing which juxtapose said first and second sensors, said first and second light transmission apertures being located so that light from said light source can pass through said light transmission apertures to said first and second sensors;

an opaque tape wound on said first and second tape reels;

first and second leader tape sections, said first and second leader tape sections being connected to each end of said opaque tape and arranged to interconnect the ends of the opaque tape to the tape reels; and first and second polarizing elements disposed in said first and second light transmission apertures respectively, each of said first and second polarizing elements being arranged to permit only light which impinges thereon from said light source to pass therethrough and to be received by one of said first and second sensors.

18. A system as claimed in claim 17 wherein each of said first and second polarizing elements are formed of alternate layers of transparent and opaque material.

19. A system as claimed in claim 17 wherein each of said first and second polarizing elements are formed of columns of transparent and opaque materials which are alternatively arranged and which are aligned with the direction in which light from said light source propagates toward each of said first and second light transmission apertures.

20. A system as claimed in claim 17 wherein each of said first and second polarizing elements is formed from a plurality of optical fibres which are bundled and secured together.

21. In a system
a light source;
first and second sensors responsive to the light emitted from said light source;
means for receiving a cassette in a manner wherein said first and second sensors proximate first and second sides of said cassette, said cassette comprising:
first and second halves which when connected together define a cassette housing;
means for defining a structure in said cassette housing which can selectively receive said light source, said structure being defined in a position essentially equidistant from the sides of said cassette housing;
means defining first and second light transmission apertures in said cassette housing which juxtapose said first and second sensors, said first and second light transmission apertures being located so that light from said light source can pass through said light transmission apertures to said first and second sensors;
an opaque tape wound on said first and second tape reels;
first and second leader tape sections, said first and second leader tape sections being connected to each end of said opaque tape and arranged to interconnect the ends of the opaque tape to the tape reels;
means defining a window in the first half, said window permitting said first and second reels to be visible from outside the cassette; and
first and second groups of corrugations formed on said second half proximate each of said first and second light transmission apertures, said first and second groups of corrugations being arranged to deflect and diffuse light which enters said cassette through said window.

22. In a tape cassette including a tape having at least one tape end having greater light transmittance than the rest of the tape, the combination of:
means for housing a light source;
means defining a light transmission aperture in a wall portion of the cassette; and
means for sensing the tape end being reached, said tape end sensing means comprising means associated with said light transmission aperture for preventing light which does not come directly from the light source from passing through said light transmission aperture, said light passage preventing means being disposed in said light transmission aperture.

23. A tape cassette as claimed in claim 22 wherein said light passage preventing means comprises a wall portion formed integrally with the cassette proximate said light transmission aperture.

24. A tape cassette as claimed in claim 22 wherein said light passage preventing means comprises two wall portions formed integrally with the cassette in close proximity to and on either side of said light transmission aperture.

25. In a tape cassette
means for housing a light source;
means defining a light transmission aperture in a wall portion of the cassette;
a tape reel on which a tape is wound, said tape having a section which is transparent to the light emitted from said light source;
means associated with said light transmission aperture for attenuating light which does not come directly from the light source and pass through said transparent section in a manner that it does not pass through said light transmission aperture and reach a sensor disposed outside of the cassette in a manner which triggers the sensor to produce a signal, said light attenuating means being disposed in said aperture.

26. A tape cassette as claimed in claim 25 wherein said light attenuating means comprises a wall portion formed integrally with the cassette proximate said light transmission aperture.

27. A tape cassette as claimed in claim 25 wherein said light attenuating means comprises two wall portions formed integrally with cassette in close proximity to and on either side of said light transmission aperture.

28. A tape cassette as claimed in claim 25 wherein said light attenuating means comprises a light polarizing element disposed in said light transmission aperture.

29. In a system
a light source;
first and second sensors responsive to the light emitted from said light source;
means for receiving a cassette in a manner wherein said first and second sensors proximate first and second sides of said cassette, said cassette comprising:
first and second halves which when connected together define a cassette housing;
first and second tape reels rotatably disposed in said cassette housing;
means for defining a structure in said cassette housing which can selectively receive said light source, said structure being defined in a position essentially equidistant from the sides of said cassette housing;
means defining first and second light transmission apertures in said cassette housing which juxtapose said first and second sensors, said first and second light transmission apertures being located so that light from said light source can pass through said light transmission apertures to said first and second sensors;
an opaque tape would be on said first and second tape reels;
first and second leader tape sections, said first and second leader tape sections being connected to each end of said opaque tape and arranged to interconnect the ends of the opaque tape to the tape reels;
first and second structures which are formed integrally with the cassette housing proximate said first and second light transmission apertures respectively;
said first and second structures attenuating light which does not come directly through said first and second leader tapes from said light source and which tends to pass through said light transmission apertures toward said sensor.

* * * * *